(12) United States Patent
Bao et al.

(10) Patent No.: US 11,544,821 B2
(45) Date of Patent: Jan. 3, 2023

(54) SYSTEMS AND METHODS FOR DETERMINING RING ARTIFACT

(71) Applicant: SHANGHAI UNITED IMAGING HEALTHCARE CO., LTD., Shanghai (CN)

(72) Inventors: Yuan Bao, Shanghai (CN); Yi Wang, Shanghai (CN); Wenjing Cao, Shanghai (CN); Xiang Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 190 days.

(21) Appl. No.: 16/862,636

(22) Filed: Apr. 30, 2020

(65) Prior Publication Data

US 2020/0380640 A1 Dec. 3, 2020

(30) Foreign Application Priority Data

Apr. 30, 2019 (CN) .......................... 201910359114.8

(51) Int. Cl.
*G06T 5/00* (2006.01)
*A61B 6/03* (2006.01)
(Continued)

(52) U.S. Cl.
CPC .............. *G06T 5/002* (2013.01); *A61B 6/032* (2013.01); *A61B 6/5258* (2013.01); *G06T 5/005* (2013.01);
(Continued)

(58) Field of Classification Search
None
See application file for complete search history.

(56) References Cited

U.S. PATENT DOCUMENTS

2008/0019607 A1* 1/2008 Star-Lack ............... G06T 5/002
382/264
2010/0215265 A1 8/2010 Tseng et al.
2010/0284599 A1* 11/2010 Fujita .................... G06T 11/005
382/131

FOREIGN PATENT DOCUMENTS

CN 102274040 A 12/2011
CN 105321155 A 2/2016
(Continued)

OTHER PUBLICATIONS

Machine translation of WO-2018103015-A1 (Year: 2018).*
(Continued)

*Primary Examiner* — Vu Le
*Assistant Examiner* — Courtney Joan Nelson
(74) *Attorney, Agent, or Firm* — Metis IP LLC

(57) ABSTRACT

The embodiments of the present disclosure disclose methods and systems for determining a ring artifact. The method for determining the ring artifact may include: obtaining an original image; mapping a plurality of pixels in the original image to a polar coordinate image; determining a protection region in the polar coordinate image; obtaining a smooth image by smoothing at least one region in the polar coordinate image other than the protection region; generating a residual image based on the polar coordinate image and the smooth image; determining a location of the ring artifact in the original image based on the residual image. In the present disclosure, the original image may be mapped to a trapezoidal region or a triangular region in the polar coordinate image, and the gradient angle image may be used for image processing, which may reduce the influence of noise. An accurate location of the ring artifact may be determined, and information for imaging device detection and air correction may be provided.

18 Claims, 14 Drawing Sheets

(51) Int. Cl.
 *A61B 6/00* (2006.01)
 *G06T 7/00* (2017.01)
 *G06T 11/00* (2006.01)
(52) U.S. Cl.
 CPC ............ *G06T 5/006* (2013.01); *G06T 7/0012* (2013.01); *G06T 11/008* (2013.01); *G06T 2207/10081* (2013.01)

(56) References Cited

FOREIGN PATENT DOCUMENTS

| | | | |
|---|---|---|---|
| CN | 106651981 A | 5/2017 | |
| CN | 109636872 A | 4/2019 | |
| DE | 102012205769 A1 * | 10/2013 | ............. A61B 6/481 |
| JP | 5597359 B2 * | 10/2014 | ............... G06T 7/73 |
| WO | WO-2018103015 A1 * | 6/2018 | ............... G06T 5/00 |

OTHER PUBLICATIONS

Machine translation of JP-5597359-B2 (Year: 2014).*
Machine translation of DE-102012205769-A1 (Year: 2013).*
Mohamed Elotmani, Abdelmajid Elmoutaouakkil, Francoise Peyrin, Mustapha Agnaou. Detection of Ring Artifacts in Computed Tomographic Images. Journal of Theoretical and Applied Information Technology, JATIT, 2016, 94 (1), pp. 84-94. hal-01998216 (Year: 2016).*
Piggott, J., & Brown, G. (2005). An introduction to polar coordinates. NRICH. Retrieved Dec. 22, 2021, from https://nrich.maths.org/2755 (Year: 2005).*

* cited by examiner

400

```
┌─────────────────────────────────────────────┐  410
│         Obtaining an original image         │
└─────────────────────────────────────────────┘
                      │
                      ▼
┌─────────────────────────────────────────────┐  420
│ Mapping a plurality of pixels in the original│
│     image to a polar coordinate image       │
└─────────────────────────────────────────────┘
                      │
                      ▼
┌─────────────────────────────────────────────┐  430
│ Determining a protection region in the polar│
│              coordinate image               │
└─────────────────────────────────────────────┘
                      │
                      ▼
┌─────────────────────────────────────────────┐  440
│ Obtaining a smooth image by smoothing at    │
│ least one region in the polar coordinate    │
│ image other than the protection region      │
└─────────────────────────────────────────────┘
                      │
                      ▼
┌─────────────────────────────────────────────┐  450
│ Generating a residual image based on the    │
│  polar coordinate image and the smooth image│
└─────────────────────────────────────────────┘
                      │
                      ▼
┌─────────────────────────────────────────────┐  460
│ Determining a location of the ring artifact │
│   in the original image based on the        │
│              residual image                 │
└─────────────────────────────────────────────┘
```

FIG. 4

SYSTEMS AND METHODS FOR DETERMINING RING ARTIFACT

CROSS-REFERENCE TO RELATED APPLICATIONS

This application claims priority of Chinese Patent Application No. 201910359114.8, filed on Apr. 30, 2019, the contents of which are hereby incorporated by reference.

TECHNICAL FIELD

The present disclosure relates to the field of image processing, and more particularly, relates to methods and systems for determining a ring artifact.

BACKGROUND

An image reconstructed by a medical imaging device (e.g., a computed tomography (CT) device, a C-arm device, etc.) usually has concentric ring artifacts, which may adversely affect the image quality. In actual use, the image may be corrected to eliminate the ring artifacts. Therefore, if a determination can be automatically made as to whether an image has a ring artifact, and a determination can then be made as to whether to correct the ring artifact in the image based on a result, it may bring a great convenience for improving the image quality.

SUMMARY

Based on this, methods, and systems for determining a ring artifact may be provided.

One aspect of the present disclosure may provide a method for determining a ring artifact. The method may include: obtaining an original image; mapping a plurality of pixels in the original image to a polar coordinate image; determining a protection region in the polar coordinate image; obtaining a smooth image by smoothing at least one region in the polar coordinate image other than the protection region; generating a residual image based on the polar coordinate image and the smooth image; determining a location of the ring artifact in the original image based on the residual image.

In some embodiments, the mapping a plurality of pixels in the original image to a polar coordinate image may include: determining a location of an imaging center in the original image; determining a plurality of rings centered on the location in the original image and from the imaging center and outward; and mapping the plurality of pixels on the plurality of rings to a plurality of lines corresponding to a plurality of rows of pixels or a plurality of columns of pixels in the polar coordinate image, respectively, wherein each of the plurality of rings may correspond to each of the plurality of rows or each of the plurality of columns.

In some embodiments, the mapping the plurality of pixels on the plurality of rings to a plurality of lines corresponding to a plurality of rows of pixels or a plurality of columns of pixels in the polar coordinate image, respectively, may include: for each ring of the plurality of rings, performing an interpolation operation on the plurality of pixels on the ring to obtain at least one interpolation pixel; mapping the plurality of pixels on the ring and the at least one interpolation pixel to a line corresponding to a row of pixels or a column of pixels in the polar coordinate image.

In some embodiments, a length of a line may positively correlate with a radius of a ring corresponding to the line.

In some embodiments, the mapping a plurality of pixels in the original image to a polar coordinate image may include: mapping the plurality of pixels in the original image to a trapezoidal region or a triangular region in the polar coordinate image.

In some embodiments, the determining a protection region in the polar coordinate image may include: obtaining a strong boundary region by performing a boundary extraction operation on the polar coordinate image.

In some embodiments, boundary extraction algorithms may include a threshold segmentation, a Laplace operator, a Sobel operator, Robert operator, a Marl operator, a Canney operator, a Shen-Castan operator, or the like, or any combination thereof.

In some embodiments, the determining a protection region in the polar coordinate image may include: generating the protection region by performing a region expansion operation on the strong boundary region.

In some embodiments, the generating a residual image based on the polar coordinate image and the smooth image may include: generating the residual image by subtracting a value of each pixel of a plurality of pixels in the polar coordinate image from a value of a corresponding pixel of a plurality of pixels in the smooth image.

In some embodiments, the determining a location of the ring artifact in the original image based on the residual image may include: determining an average value of each row of a plurality of rows of pixels in the residual image, or an average value of each column of a plurality of columns of pixels in the residual image; determining a ring in the original image corresponding to a row or a column in the residual image whose average value is greater than a first threshold or below a second threshold as a ring artifact region.

In some embodiments, the determining a location of the ring artifact in the original image based on the residual image may include: generating a gradient angle image based on the residual image; determining an average value of each row of a plurality of rows of pixels in the gradient angle image, or an average value of each column of a plurality of columns of pixels in the residual image; determining a row with a peak value or a valley value, or a column with the peak value or the valley value, wherein the peak value is the average value greater than a third threshold, and the valley value is the average value less than a fourth threshold; determining the row or the column with the peak value, and a row or a column with the valley value that is closest to the row or the column with the peak value, as a peak-valley position pair; selecting a peak-valley position pair with a row distance between the row with the peak value and the row with the valley value less than a preset distance threshold, or a column distance between the column with the peak value and the column with the valley value less than the preset distance threshold; determining a ring artifact region in the original image based on a ring corresponding to the rows or the columns of the selected peak-valley position pair.

In some embodiments, the generating a gradient angle image based on the residual image may include obtaining the gradient angle image by determining a gradient angle value of each pixel of a plurality of pixels in the residual image, wherein the gradient angle value may reflect a ratio of a change in pixel values along each of at least two different directions in the residual image.

One aspect of the present disclosure may provide a system for determining a ring artifact. The system may include an obtaining module, a mapping module, a protection region determination module, a smoothing module, a residual image generation module, and a ring artifact determination module. The obtaining module may be configured to obtain an original image. The mapping module may be configured to map a plurality of pixels in the original image to a polar coordinate image. The protection region determination module may be configured to determine a protection region in the polar coordinate image. The smoothing module may be configured to obtain a smooth image by smoothing at least one region in the polar coordinate image other than the protection region. The residual image generation module may be configured to generate a residual image based on the polar coordinate image and the smooth image. The ring artifact determination module may be configured to determine a location of the ring artifact in the original image based on the residual image.

One aspect of the present disclosure may provide a device for determining a ring artifact. The device may include at least one processor and at least one storage device configured to store a set of instructions that, when executing the set of instructions, causes the at least one processor to perform a method for determining the ring artifact as described in some embodiments of the present disclosure.

One aspect of the present disclosure may provide a computer readable storage medium. The storage medium may store computer instructions, the instructions, when executed by the computer, causing the computer to implement a method for determining the ring artifact as described in some embodiments of the present disclosure.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein:

FIG. 4 is a flowchart illustrating an exemplary process for determining a ring artifact according to some embodiments of the present disclosure;

DETAILED DESCRIPTION

Figure 1:
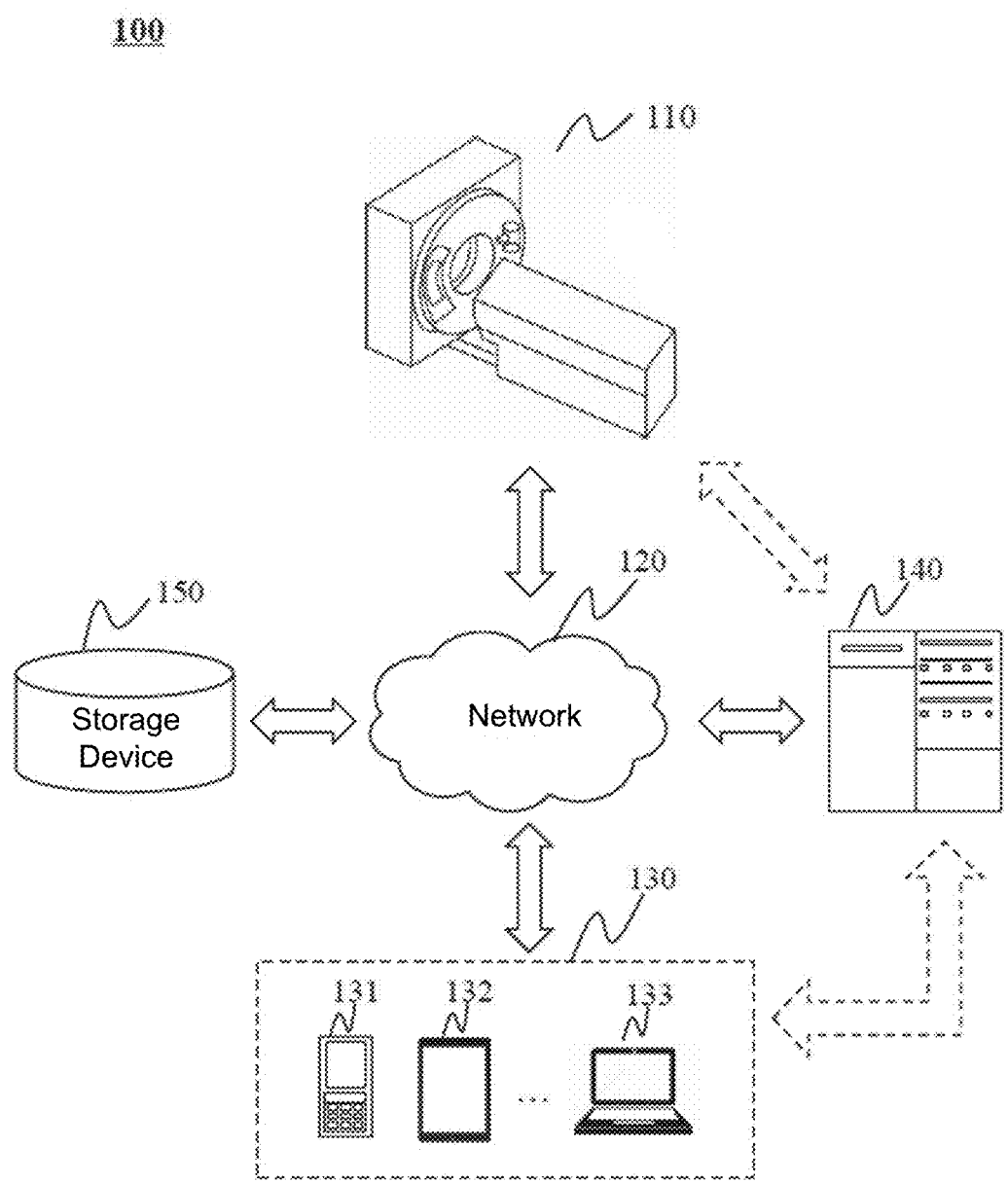
FIG. 1 is a schematic diagram illustrating an exemplary imaging system according to some embodiments of the present disclosure.

In order to illustrate the technical solutions related to the embodiments of the present disclosure, a brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless apparent from the locale or otherwise stated, like reference numerals represent similar structures or operation throughout the several views of the drawings.

It will be understood that the term "system," "device," "unit," and/or "module" used herein are one method to distinguish different components, elements, parts, section, or assembly of different level in ascending order. However, the terms may be displaced by another expression if they achieve the same purpose.

As used in the disclosure and the appended claims, the singular forms "a," "an," and "the" include plural referents unless the content clearly dictates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

These and other features, and characteristics of the present disclosure, as well as the methods of operations and functions of the related elements of structure and the combination of parts and economies of manufacture, may become more apparent upon consideration of the following description with reference to the accompanying drawings, all of which form part of this disclosure. It is to be expressly understood, however, that the drawings are for the purpose of illustration and description only and are not intended to limit the scope of the present disclosure. It is understood that the drawings are not to scale.

FIG. 1 is a schematic diagram illustrating an exemplary imaging system 100 according to some embodiments of the present disclosure.

The imaging system 100 may include an imaging device 110, a network 120, a processing device 140, and a storage device 150. In some embodiments, the imaging system 100 may further include at least one terminal 130. Components in the imaging system 100 may be connected to each other through the network 120. For example, the imaging device 110 may be connected to or communicate with the at least one terminal 130 through the network 120.

In some embodiments, the imaging device 110 may obtain scan data of a subject by scanning the subject in a detection region. In some embodiments, the imaging device 110 may be configured to obtain medical image data. The subject to be scanned may be a whole or a part of an organ or tissue of a human body or an animal, such as the head, etc. In some embodiments, the imaging device 110 may be configured to obtain industrial image data. The subject to be scanned may be a workpiece. In some embodiments, the imaging device 110 may be an X-ray imaging device, such as a computed tomography scanner (CT), a C-arm, or the like.

The network 120 may include any suitable network that can facilitate exchange of information and/or data of the imaging system 100. In some embodiments, at least one component of the imaging system 100 (e.g., the imaging device 110, the processing device 140, the storage device 150, the at least one terminal 130) may communicate information and/or data with at least one other component of the imaging system 100 via the network 120. For example, the processing device 140 may obtain an image outputted from the imaging device 110 via the network 120. As another example, the processing device 140 may obtain a user (e.g., a doctor) instruction from the at least one terminal 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, a router, a hub, a switch, a server computer, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include at least one network access point. For example, the network 120 may include a wired and/or wireless network access point such as a base station and/or an internet exchange point through which at least one component of the imaging system 100 may be connected to the network 120 to exchange data and/or information.

The at least one terminal 130 may be connected to and/or communicate with the imaging device 110, the processing device 140, and/or the storage device 150. For example, the at least one terminal 130 may obtain a detected image from the processing device 140. As another example, the at least one terminal 130 may obtain an output image obtained by the imaging device 110, and send the output image to the processing device 140 for processing. In some embodiments, the at least one terminal 130 may include a mobile device 131, a tablet computer 132, a laptop computer 133, or the like, or any combination thereof. For example, the mobile device 131 may include a mobile phone, a personal digital assistance (PDA), a gaming device, a navigation device, a point of sale (POS) device, or the like, or any combination thereof. In some embodiments, the at least one terminal 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. Input information received through the input device may be transmitted to the processing device 140 via, for example, a bus, for further processing. Other types of the input device may include a cursor control device, such as a mouse, a trackball, a cursor direction key, etc. The output device may include a display, a speaker, a printer, or the like, or any combination thereof. In some embodiments, the at least one terminal 130 may be part of the processing device 140.

The processing device 140 may process data and/or information obtained from the imaging device 110, the storage device 150, the at least one terminal 130, or other components of the imaging system 100. For example, the processing device 140 may obtain an original image from the imaging device 110 and determine an artifact in the original image, such as a ring artifact. In some embodiments, the processing device 140 may be a single server or a server group. The server group may be centralized or distributed. In some embodiments, the processing device 140 may be local or remote. For example, the processing device 140 may access information and/or data from the imaging device 110, the storage device 150, and/or the at least one terminal 130 via the network 120. As another example, the processing device 140 may be directly connected to the imaging device 110, the at least one terminal 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by the computing device 200.

The storage device 150 may store data, instructions, and/or any other information. In some embodiments, the storage device 150 may store an image, e.g., an original image, outputted from the imaging device 110. In some embodiments, the storage device 150 may store data obtained from the imaging device 110, the at least one terminal 130, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-write memory may include a random-access memory (RAM). Exemplary RAM may include a dynamic RAM (DRAM), a double date rate synchronous dynamic RAM (DDRSDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform.

In some embodiments, the storage device 150 may be connected to the network 120 to communicate with at least one other component of the imaging system 100 (e.g., the processing device 140, the at least one terminal 130). At least one component of the imaging system 100 may access data or instructions stored in the storage device 150 via the network 120. In some embodiments, the storage device 150 may be part of the processing device 140.

It should be noted that the above description is merely provided for the purpose of illustration, and not intended to limit the scope of the present disclosure. For persons having ordinary skills in the art, multiple variations and modifications may be made under the teachings of the present disclosure. The features, structures, methods, and other characteristics of the exemplary embodiments described herein may be combined in various ways to obtain additional and/or alternative exemplary embodiments. For example, the storage device 150 may be a data storage including a cloud computing platform, such as a public cloud, a private cloud, a community cloud, and a hybrid cloud, etc. However, those variations and modifications do not depart from the scope of the present disclosure.

Figure 2:
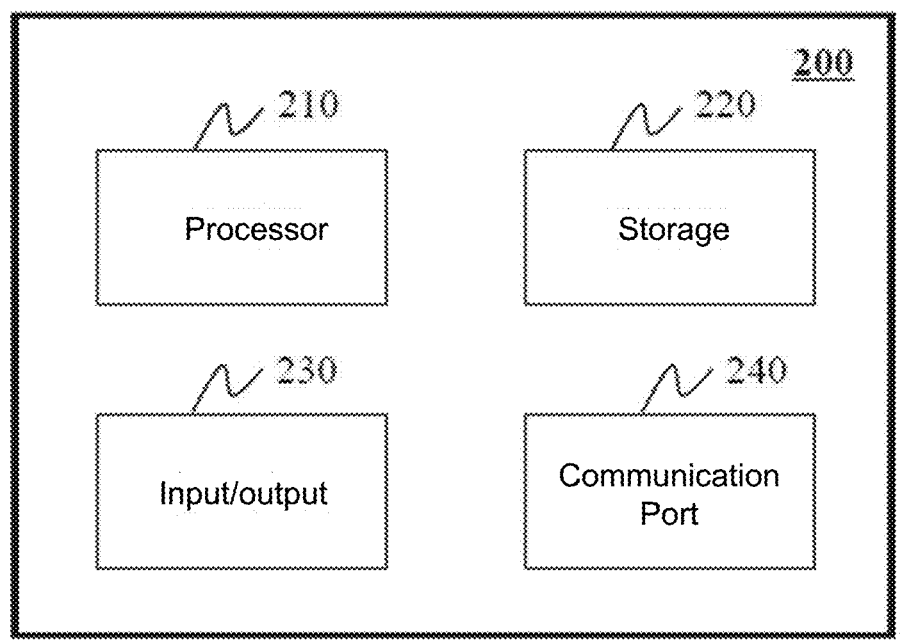
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device 200.

The computing device 200 may include a processor 210, a storage 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, data structures, procedures, modules, and functions, which perform particular functions described herein. For example, the processor 210 may process data of the imaging device 110, the at least one terminal 130, the storage device 150, and/or any other components of the imaging system 100. In some embodiments, the processor 210 may include at least one hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the at least one terminal 130, the storage device 150, and/or any other components of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDRSDRAM), a static RAM (SRAM), a thyristor RAM (T-RAM), and a zero-capacitor (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store at least one program and/or instruction to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or any combination thereof. Exemplary output devices may include a display device, a loudspeaker, a printer, a projector, or the like, or any combination thereof. Exemplary display devices may include a liquid crystal display (LCD), a light-emitting diode (LED)-based display, a flat panel display, a curved screen, a television device, a cathode ray tube, or the like, or any combination thereof.

The communication port 240 may be connected to a network (e.g., the network 120) to facilitate data communications. The communication port 240 may establish connections between the processing device 140 and the imaging device 110, the terminals 130, and/or the storage device 150. The connection may include a wired connection or a wireless connection. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
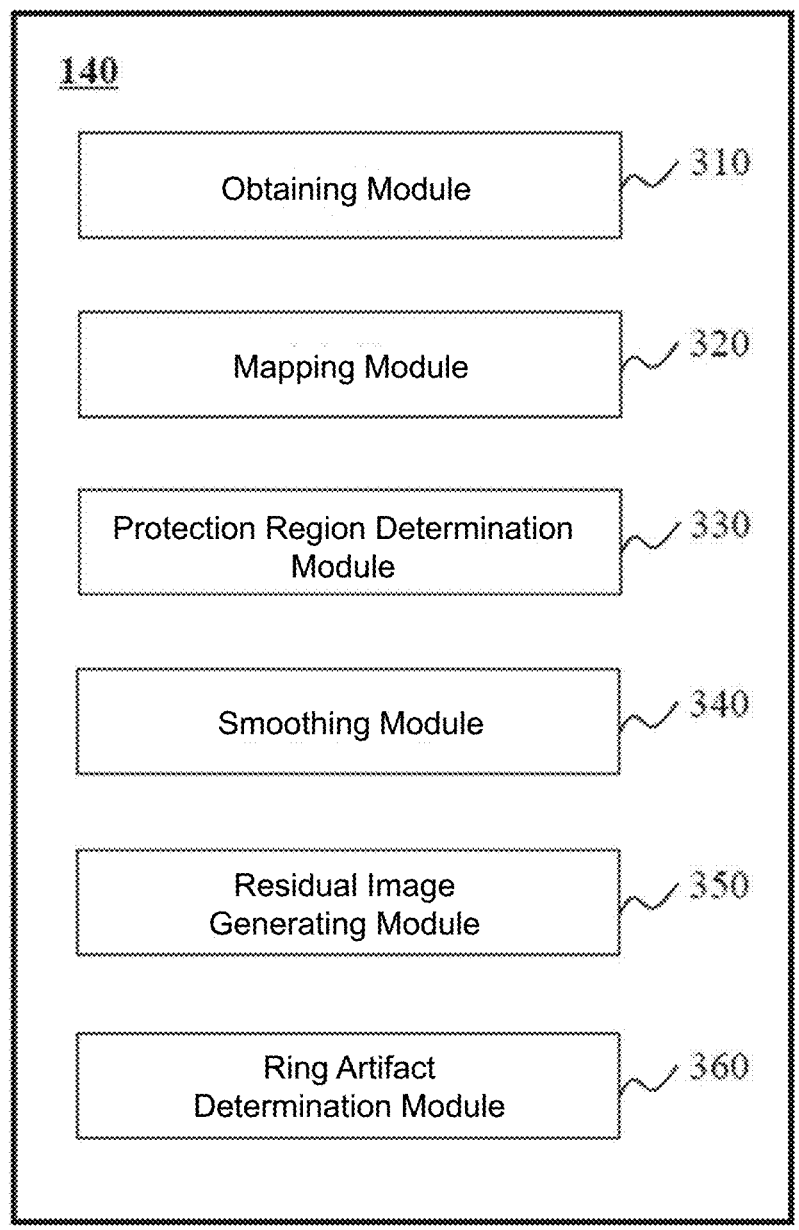
FIG. 3 is an exemplary block diagram illustrating a processing device according to some embodiments of the present disclosure.

FIG. 3 is an exemplary block diagram illustrating a processing device according to some embodiments of the present disclosure.

As shown in FIG. 3, a processing device 140 may include an obtaining module 310, a mapping module 320, a protection region determination module 330, a smoothing module 340, a residual image generation module 350, and a ring artifact determination module 360. The obtaining module 310 may be configured to obtain an image. Specifically, the obtaining module 310 may be configured to obtain an original image. In some embodiments, the original image may be an image captured at a current time, or an image captured at a historical time and stored in a storage device (e.g., the storage device 150). In some embodiments, the original image may be an image corresponding to a human body region (e.g., the chest, the head, an arm, the waist, a knee joint, etc.).

The mapping module 320 may be configured to map a pixel. Specifically, the mapping module 320 may map a pixel in an original image to a polar coordinate image. In some embodiments, the mapping module 320 may determine a location of an imaging center in the original image; determine a plurality of rings centered on the location in the original image and from the imaging center and outward; map a plurality of pixels on the plurality of rings to a plurality of lines corresponding to a plurality of rows of pixels or a plurality of columns of pixels in the polar coordinate image, respectively. Each of the plurality of rings may correspond to each of the plurality of rows or each of the plurality of columns. In some embodiments, the mapping module 320 may map the plurality of pixels in the original image to a trapezoidal region or a triangular region in the polar coordinate image.

The protection region determination module 330 may be configured to determine a protection region in an image. Specifically, the protection region determination module 330 may be configured to determine a protection region in a polar coordinate image. In some embodiments, the protection region determination module 330 may obtain a strong boundary region by performing a boundary extraction operation on the polar coordinate image. In some embodiments, the protection region determination module 330 may generate a protection region by performing a region expansion operation on the strong boundary region.

The smoothing module 340 may be configured to smooth a region in an image to obtain a smooth image. Specifically, the smoothing module 340 may be configured to obtain a smooth image by smoothing at least one region in a polar coordinate image other than a protection region. In some embodiments, a smooth processing-technique may include a box filtering technique, a mean filtering-technique, a Gaussian filtering technique, a neighborhood averaging technique, a median filtering technique, a bilateral filtering technique, a guided filtering technique, or the like.

The residual image generation module 350 may be configured to generate a residual image. Specifically, the residual image generation module 350 may be configured to generate a residual image based on a polar coordinate image and a smooth image. In some embodiments, the residual image generation module 350 may generate a residual image by subtracting a value of each pixel of a plurality of pixels in a polar coordinate image from a value of a corresponding pixel of a plurality of pixels in a smooth image.

The ring artifact determination module 360 may be configured to determine a location of a ring artifact in an original image. Specifically, the ring artifact determination module 360 may be configured to determine a location of a ring artifact in an original image based on a residual image. In some embodiments, the ring artifact determination module 360 may determine an average value of each row of a plurality of rows of pixels in the residual image, or an average value of each column of a plurality of columns of pixels in the residual image; determine a ring in the original image corresponding to a row or a column in the residual image whose average value is greater than a first threshold or below a second threshold as a ring artifact region. In some embodiments, the ring artifact determination module 360 may generate a gradient angle image based on the residual image; determine an average value of each row of a plurality of rows of pixels in the gradient angle image, or an average value of each column of a plurality of columns of pixels in the residual image; determine a row with a peak value or a valley value, or a column with the peak value or the valley value, wherein the peak value may be the average value greater than a third threshold, and the valley value may be the average value less than a fourth threshold; determine the row or the column with the peak value, and a row or a column with the valley value that is closest to the row or the column with the peak value, as a peak-valley position pair; select a peak-valley position pair with a row distance between the row with the peak value and the row with the valley value less than a preset distance threshold, or a column distance between the column with the peak value and the column with the valley value less than the preset distance threshold; determine a ring artifact region in the original image based on a ring corresponding to the rows or the columns of the selected peak-valley position pair.

FIG. 4 is a flowchart illustrating an exemplary process for determining a ring artifact according to some embodiments of the present disclosure. Specifically, the ring artifact determination process 400 may be performed by the processing device 140. For example, the ring artifact determination process 400 may be stored in a storage device (e.g., the storage device 150, the storage 220) in the form of a program or an instruction. When the imaging system 100 (e.g., the processing device 140) executes the program or the instruction, the ring artifact determination process 400 may be implemented. As shown in FIG. 4, the ring artifact determination process 400 may include:

In 410, an original image may be obtained. Specifically, operation 410 may be performed by the obtaining module 310.

Figure 7:
FIG. 7 is a schematic diagram illustrating an original image according to some embodiments of the present disclosure.

In some embodiments, the original image may be an output image of the imaging device 110. In some embodiments, the output image may be the latest output image of the imaging device 110, or other output image during an imaging process. In some embodiments, the original image may be an image corresponding to a body part of a human. In some embodiments, the body part may be tissue, an organ, and/or a body part of a subject. Specifically, the tissue may include but not limited to muscle tissue, nerve tissue, bone tissue, epithelial tissue, etc. The organ may include but not limited to the heart, a liver, a lung, the stomach, a kidney, etc. The body part may include but not limited to the head, a hand, an arm, a foot, a calf, a thigh, the abdomen, the chest, etc. Merely by way of example, the obtaining module 310 may obtain the original image as shown in FIG. 7.

In some embodiments, an instruction to obtain the original image may be stored in a storage device (e.g., the storage device 150, the storage 220), and may be retrieved by the processing device 140 (e.g., the obtaining module 310).

In 420, a plurality of pixels in the original image may be mapped to a polar coordinate image. Specifically, operation 420 may be performed by the mapping module 320.

In some embodiments, the pixel in the original image may have pixel information. In some embodiments, the pixel information may include a coordinate value and a pixel value (or an image value) in the original image. The pixel value may include a brightness value, a gray value, a CT value, an RGB value, a contrast, a signal-to-noise ratio, etc. In some embodiments, the pixel in the polar coordinate image may have pixel information. In some embodiments, the pixel information may include a coordinate value and a pixel value (or an image value) in the polar coordinate image. The pixel value may include a grayscale value, a brightness value, a CT value, an RGB value, a contrast, a signal-to-noise ratio, etc.

In some embodiments, the pixel in the original image may be mapped or migrated to a new location in the polar coordinate image by transforming a coordinate location of the pixel in the original image, to obtain the polar coordinate image. It should be understood that the pixel in the original image may correspond to a corresponding pixel in the polar coordinate image. The pair of pixels may have a same pixel value, but may have different coordinate locations in respective images. Merely by way of example, a pixel a in the original image may correspond to a pixel b in the polar coordinate image, and the pixel value of the pixel a may be the same as the pixel value of the pixel b. A coordinate location of the pixel a in the original image may be row 24 and column 30, and a coordinate location of the pixel b in the original image may be row 2 and column 28. In some embodiments, the pixels on the rings centered on a location of an imaging center in the original image and from the imaging center and outward, may be mapped to rows of pixels in the polar coordinate image. The rings in the original image may correspond to the rows in the polar coordinate image, respectively. In some embodiments, the rows from top to bottom in the polar coordinate image may correspond to the rings from the imaging center to outward in the original image, respectively. In some embodiments, the pixels on the rings in the original image may be mapped to columns of pixels in the polar coordinate image. The rings in the original image may correspond to the columns in the polar coordinate image, respectively. In some embodiments, the coordinate location of the pixel in the original image may be transformed according to other rules to map the pixel to the polar coordinate image, and not limited to those exemplified herein.

Figure 8:
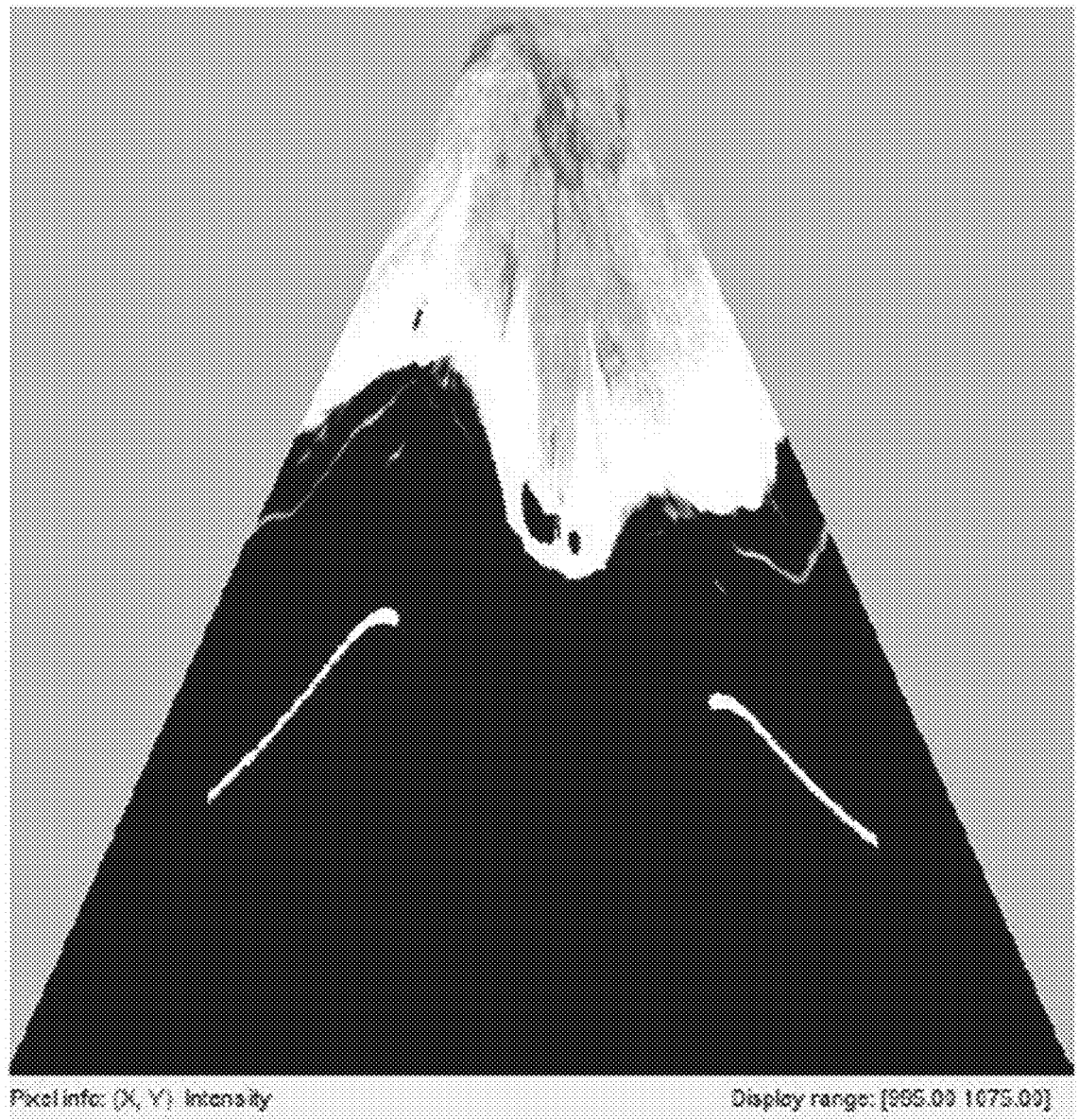
FIG. 8 is a schematic diagram illustrating a polar coordinate image according to some embodiments of the present disclosure.

In some embodiments, after the pixels in the original image are mapped to the polar coordinate image, a trapezoidal region or a triangular region may be formed. In some embodiments, the trapezoid may be an isosceles trapezoid or a non-isosceles trapezoid. In some embodiments, the triangle may be an isosceles triangle, an equilateral triangle, or an unequal triangle. In some embodiments, the pixels in the original image may be mapped to the trapezoidal region or the triangular region in the polar coordinate image. Merely by way of example, the mapping module 320 may map the pixels in the original image to a polar coordinate image as shown in FIG. 8. In the polar coordinate image, only the pixel in the trapezoidal region in the polar coordinate image may have a pixel value. The pixel value of the pixel in a background region other than the trapezoidal region may be regarded as an invalid value, and may not affect a result of a subsequent image processing operation. In some embodiments, the pixel value of the pixel in the background region other than the trapezoidal region may be set as 0. More descriptions of the mapping process of the polar coordinate image may be found elsewhere in the present disclosure (e.g., FIG. 5 and description thereof), and are not repeated here.

In some embodiments, an instruction to map the polar coordinate image may be stored in a storage device (e.g., the storage device 150, the storage 220), and may be retrieved by the processing device 140 (e.g., the mapping module 320).

In 430, a protection region in the polar coordinate image may be determined. Specifically, operation 430 may be performed by the protection region determination module 330.

Figure 9:
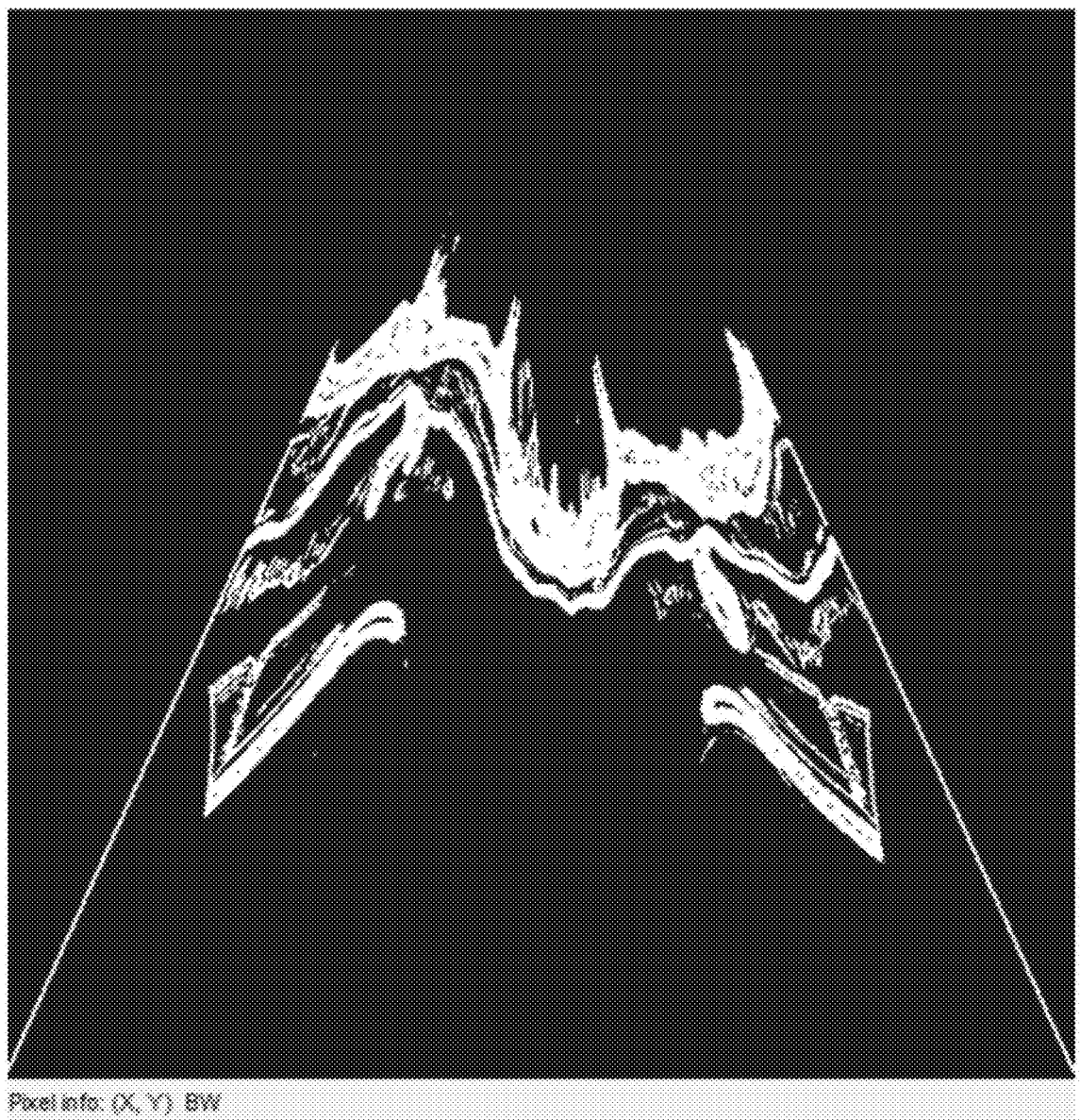
FIG. 9 is a schematic diagram illustrating a strong boundary region image according to some embodiments of the present disclosure.

In some embodiments, a boundary extraction operation may be performed on the polar coordinate image to obtain a strong boundary region. In some embodiments, the strong boundary region may be determined as the protection region, and a pixel in the protection region may not be processed. In some embodiments, the strong boundary region may be a region corresponding to a high density of human tissue in the polar coordinate image, that is, a region with a high CT value, such as a region corresponding to a bone in the polar coordinate image. In some embodiments, boundary extraction techniques may include a threshold segmentation, a Laplace operator, a Sobel operator, a Robert operator, a Marl operator, a Canney operator, a Shen-Castan operator, or the like, or any combination thereof. Specifically, a boundary corresponding to the high density of human tissue in the polar coordinate image may be extracted according to the boundary extraction technique, to obtain the strong boundary region. In some embodiments, a region expansion operation may be performed on the strong boundary region, and the strong protection region and an expanded region may be determined as the protection region. In some embodiments, the region expansion operation may include expanding from the strong boundary to a region outside the strong boundary. An expanded strong boundary region may be determined as the protection region. Specifically, a specific count of pixels (e.g., 5 pixels, 6 pixels, 7 pixels, 8 pixels) may be expanded outward from the pixels on the strong boundary as starting points, and the specific count of pixels beyond the strong boundary region may be assigned into the strong boundary region. The protection region may include the expanded region and the original strong boundary region. Merely by way of example, the protection region determination module 330 may determine the protection region in the polar coordinate image as shown in FIG. 9.

In some embodiments, an instruction to determine the protection region may be stored in a storage device (e.g., the storage device 150, the storage 220) and may be retrieved by the processing device 140 (e.g., the protection region determination module 330).

In 440, a smooth image may be obtained by smoothing at least one region in the polar coordinate image other than the protection region. Specifically, operation 440 may be performed by the smoothing module 340.

Figure 10:
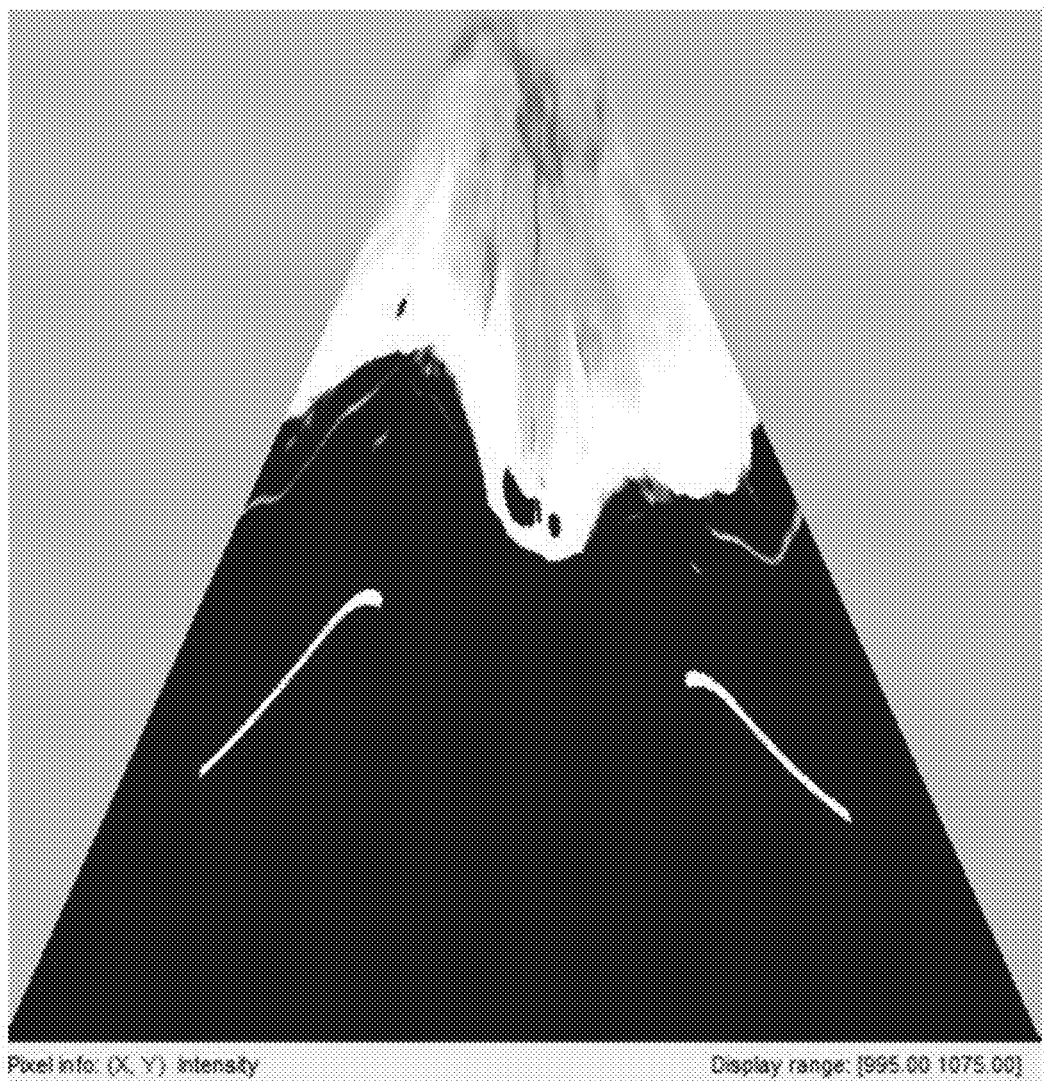
FIG. 10 is a schematic diagram illustrating a smooth image according to some embodiments of the present disclosure.

In some embodiments, the region other than protection region may include a background region and a human tissue region. In some embodiments, the human tissue region other than the protection region may be a region corresponding to a low density of human tissue in the polar coordinate image, that is, a region with a low CT value, such as a region corresponding to human muscle tissue, brain marrow tissue, nerve tissue, etc., in the polar coordinate image. In some embodiments, a smooth processing operation may be performed on the region in the polar coordinate image other than the protection region. Merely by way of example, when the smooth processing operation is performed on the polar coordinate image, a determination may be made as to whether a pixel involved in the smooth processing operation belongs to the protection region. For example, a determination may be made as to whether a coordinate location of the pixel is within the protection region as shown in FIG. 9. If the coordinate location of the pixel is within the protection region, the pixel may be removed from the smooth processing operation, and the remaining pixels may be operated similarly. In some embodiments, the smooth processing operation may be performed on a region in the polar coordinate image other than the protection region and the background region. It should be understood that the smooth processing operation may be performed on a region corresponding to human tissue other than the protection region. In some embodiments, smooth processing techniques may include a box filtering technique, a mean filtering technique, a Gaussian filtering technique, a neighborhood averaging technique, a median filtering technique, a bilateral filtering technique, a guided filtering technique, or the like. Merely by way of example, the smoothing module 340 may smooth a region in the polar coordinate image other than the protection region, to obtain a smooth image as shown in FIG. 10. In the smooth image shown in FIG. 10, a pixel value of a pixel in the protection region shown in FIG. 9 may remain an original pixel value (i.e., corresponds to a pixel value shown in FIG. 8).

In some embodiments, an instruction to perform a smooth processing operation may be stored in a storage device (e.g., the storage device 150, the storage 220) and may be retrieved by the processing device 140 (e.g., the smoothing module 340).

In 450, a residual image may be generated based on the polar coordinate image and the smooth image. Specifically, operation 450 may be performed by the residual image generation module 350.

Figure 11:
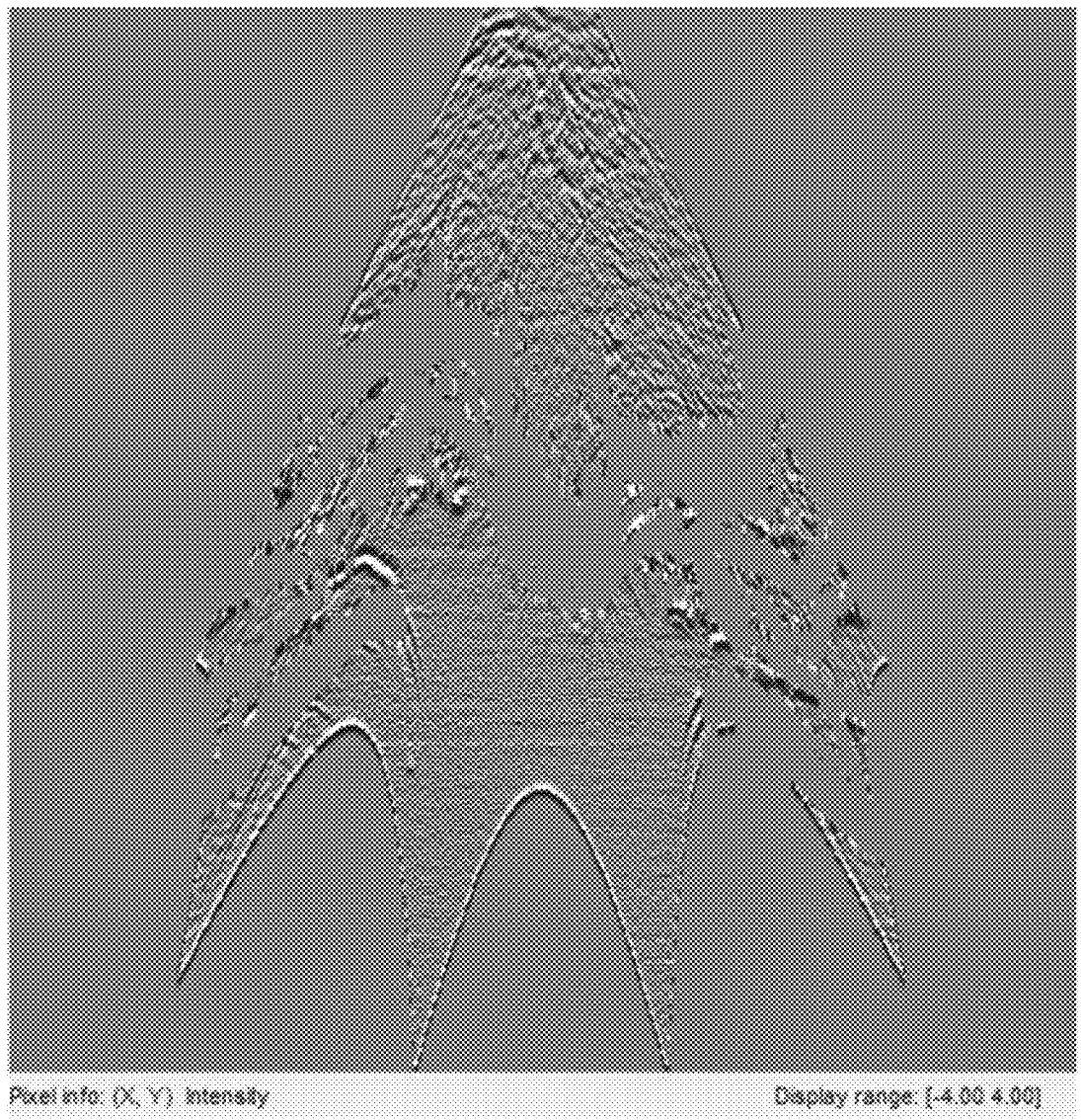
FIG. 11 is a schematic diagram illustrating a residual image according to some embodiments of the present disclosure.

In some embodiments, the residual image may be an image generated by subtracting a value of each pixel of a plurality of pixels in the polar coordinate image from a value of a corresponding pixel of a plurality of pixels in the smooth image. Merely by way of example, the residual image generation module 350 may generate a residual image as shown in FIG. 11 based on the polar coordinate image and the smooth image. A pixel value of a pixel in the residual image in the protection region shown in FIG. 9 may be 0.

In some embodiments, an instruction to generate a residual image may be stored in a storage device (e.g., the storage device 150, the storage 220), and may be retrieved by the processing device 140 (e.g., the residual image generation module 350).

In 460, a location of a ring artifact in the original image may be determined based on the residual image. Specifically, operation 460 may be performed by the ring artifact determination module 360.

In some embodiments, determining the location of the ring artifact in the original image may include determining an average value of each row of a plurality of rows of pixels in the residual image, or an average value of each column of a plurality of columns of pixels in the residual image, and determining the location of the artifact ring based on the average value. Take a process for determining the average value of the each row of the plurality of rows of pixels in the residual image as an example. It should be understood that, in some other embodiments, the location of the artifact ring may be determined based on the average value of the each row of the plurality of rows of pixels in the residual image. Specifically, the average value of pixels values of the each row of the plurality of rows of pixels in the residual image may be determined. In some embodiments, the ring artifact may be a bright ring or a dark ring of a certain width. In some embodiments, a ring in the original image corresponding to a row in the residual image whose average value is greater than a first threshold may be determined as a ring artifact region, e.g., a bright ring. As another example, a ring in the original image corresponding to a row in the residual image whose average value is below a second threshold may be determined as the ring artifact region, e.g., a dark ring. In some embodiments, the first threshold and the second threshold may be preset by an operator (e.g., a doctor) based on experiences. In some embodiments, the first threshold and the second threshold may have a same absolute value, and the two thresholds may be opposite numbers. In some embodiments, the count of rows in the residual image whose average value satisfies a preset condition may be one or more, and the count of corresponding rings in the original image may be one or more. That is, the ring artifact region may include one or more ring artifacts. In some embodiments, a summation operation may be performed on the each row or each column in the residual image. The location of the artifact ring may be determined based on a summation result. In some embodiments, the residual image may further be processed, and the location of the ring artifact in the original image may be determined based on a processed residual image. More descriptions of alternative processes may be found elsewhere in the present disclosure (e.g. FIG. 6 and description thereof), and are not repeated here.

In some embodiments, an instruction to determine the location of the ring artifact may be stored in a storage device (e.g., the storage device 150, the storage 220), and may be retrieved by the processing device 140 (e.g., the ring artifact determination module 360).

It should be noted that process 400 and the description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the pixels in the original image may be mapped to a parallelogram region in the polar coordinate image.

Figure 5:
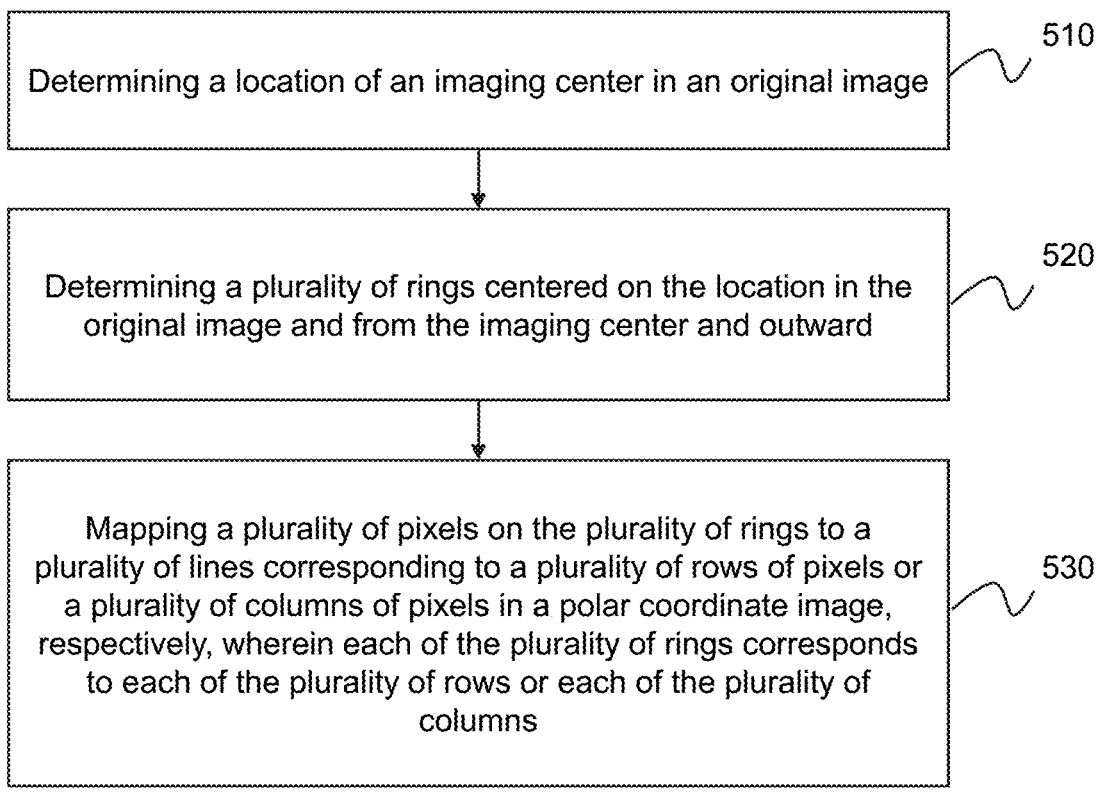
FIG. 5 is a flowchart illustrating an exemplary process for mapping a polar coordinate image according to some embodiments of the present disclosure.

FIG. 5 is a flowchart illustrating an exemplary process 500 for mapping a polar coordinate image according to some embodiments of the present disclosure. Specifically, process 500 for mapping the polar coordinate image may be executed by the processing device 140. For example, process 500 for mapping the polar coordinate image may be stored in a storage device (e.g., the storage device 150, the storage 220) in the form of a program or an instruction. When the imaging system 100 (e.g., the processing device 140) executes the program or the instruction, process 500 for mapping the polar coordinate image may be implemented. As shown in FIG. 5, process 500 for mapping the polar coordinate image may include:

In 510, a location of an imaging center in the original image may be determined. Specifically, operation 510 may be performed by the mapping module 320.

In some embodiments, the imaging center may be a scanning center of the imaging device 110, such as a rotation center of a gantry when a CT device scans. In some embodiments, the imaging center may be a geometric center of the original image or other locations in the original image. The imaging center may be designated by an operator (e.g., a doctor) of the imaging device 110. In some embodiments, the location of the imaging center in the original image may be recorded by the imaging device 110, outputted and displayed in the original image. In some embodiments, the location of the imaging center in the original image may be a coordinate value, e.g., X=50 mm and Y=55 mm, in a Cartesian coordinate system.

In some embodiments, an instruction to determine the location of the imaging center may be stored in a storage device (e.g., the storage device 150, the storage 220), and may be retrieved by the processing device 140 (e.g., the mapping module 320).

In 520, a plurality of rings centered on the location in the original image and from the imaging center and outward may be determined. Specifically, operation 520 may be performed by the mapping module 320.

In some embodiments, the plurality of rings may be a plurality of circular rings. The radii of the plurality of circular rings may increase successively from the imaging center outward. In some embodiments, spacings between adjacent circular rings of the plurality of circular rings may be the same or different. In some embodiments, a width of a circular ring may be one pixel. In some embodiments, all pixels in the original image may be located on the plurality of circular rings. In some embodiments, pixels on one circular ring may form a substantially continuous circular ring, or multiple arcs (e.g., one arc, two arcs, three arcs, four arcs).

In some embodiments, an instruction to determine the plurality of rings in the original image may be stored in a storage device (e.g., the storage device 150, the storage 220), and may be retrieved by the processing device 140 (e.g., the mapping module 320).

In 530, a plurality of pixels on the plurality of rings may be mapped to a plurality of lines corresponding to a plurality of rows of pixels or a plurality of columns of pixels in the polar coordinate image, respectively. Each of the plurality of rings may correspond to each of the plurality of rows or each of the plurality of columns. Specifically, operation 530 may be performed by the mapping module 320.

In some embodiments, the pixels on the plurality of rings may be mapped to the plurality of lines corresponding to the plurality of rows of pixels or the plurality of columns of pixels in the polar coordinate image, respectively. Each of the plurality of rings may correspond to each of the plurality of rows or each of the plurality of columns. In some embodiments, a length of the plurality of lines corresponding to the plurality of rows may gradually increase from top to bottom or from bottom to top. In some embodiments, the length of the plurality of lines corresponding to the plurality of columns may gradually increase from left to right or from right to left. In some embodiments, the length of the plurality of lines corresponding to the plurality of rows or the plurality of columns may be preset. In some embodiments, the plurality of lines corresponding to the plurality of rows or the plurality of columns may form a trapezoidal region or a triangular region. In some embodiments, the length of the line may positively correlate with a radius of the ring corresponding to the line.

In some embodiments, the count of pixels on the ring in the original image may be relatively small, e.g., on a ring close to the imaging center. At this time, after the pixels on the ring are mapped on the polar coordinate image, a formed line may be relatively short, or the pixels on the line may be relatively sparse. Therefore, for each ring of the plurality of rings, an interpolation operation may be performed on the plurality of pixels on the ring to obtain at least one interpolation pixel. The plurality of pixels on the ring and the at least one interpolation pixel may be mapped to the line corresponding to the row of pixels or the column of pixels in the polar coordinate image. In some embodiments, the length of the line corresponding to the row of or the column may be preset, and the count of interpolation pixel(s) may be determined based on the length of the line. Specifically, the imaging center in the original image may be set as an origin of a coordinate system. A direction of the row of the original image from left to right may be a positive X axis. A direction of the column of the original image from bottom to top may be a positive Y axis. An intersection of the ring and the positive X axis may be determined as a first pixel. The pixels may be successively numbered counterclockwise. The interpolation operation may be performed based on the length of the line corresponding to the row of or the column. For example, according to a ratio of spacings between adjacent pixels on the ring, the pixels may be arranged in sequence from one end of the line to the other end of the line based on the length of the line corresponding to the row. A sparse or missing part of the pixels on the ring may be interpolated correspondingly. In some embodiments, the pixel value of the interpolation pixel may be a mean value of the pixel values of all pixels on the ring (e.g., an arithmetic mean value, a weighted mean value), or a value obtained by other operation manners (e.g., a median value, a regional mean value obtained after fitting, etc.) In some embodiments, the pixel value of the interpolation pixel may also be obtained by an interpolation manner such as a nearest neighbor interpolation, a bilinear interpolation, a bicubic interpolation, etc.

In some embodiments, an instruction to map pixels on the ring to the line may be stored in a storage device (e.g., the storage device 150, the storage 220), and may be retrieved by the processing device 140 (e.g., the mapping module 320).

It should be noted that process 500 and the description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in 530, the pixels on the ring may be directly mapped to the line corresponding to the row or the column in the polar coordinate image, and an interpolation operation may be performed on the line in the polar coordinate image.

Figure 6:
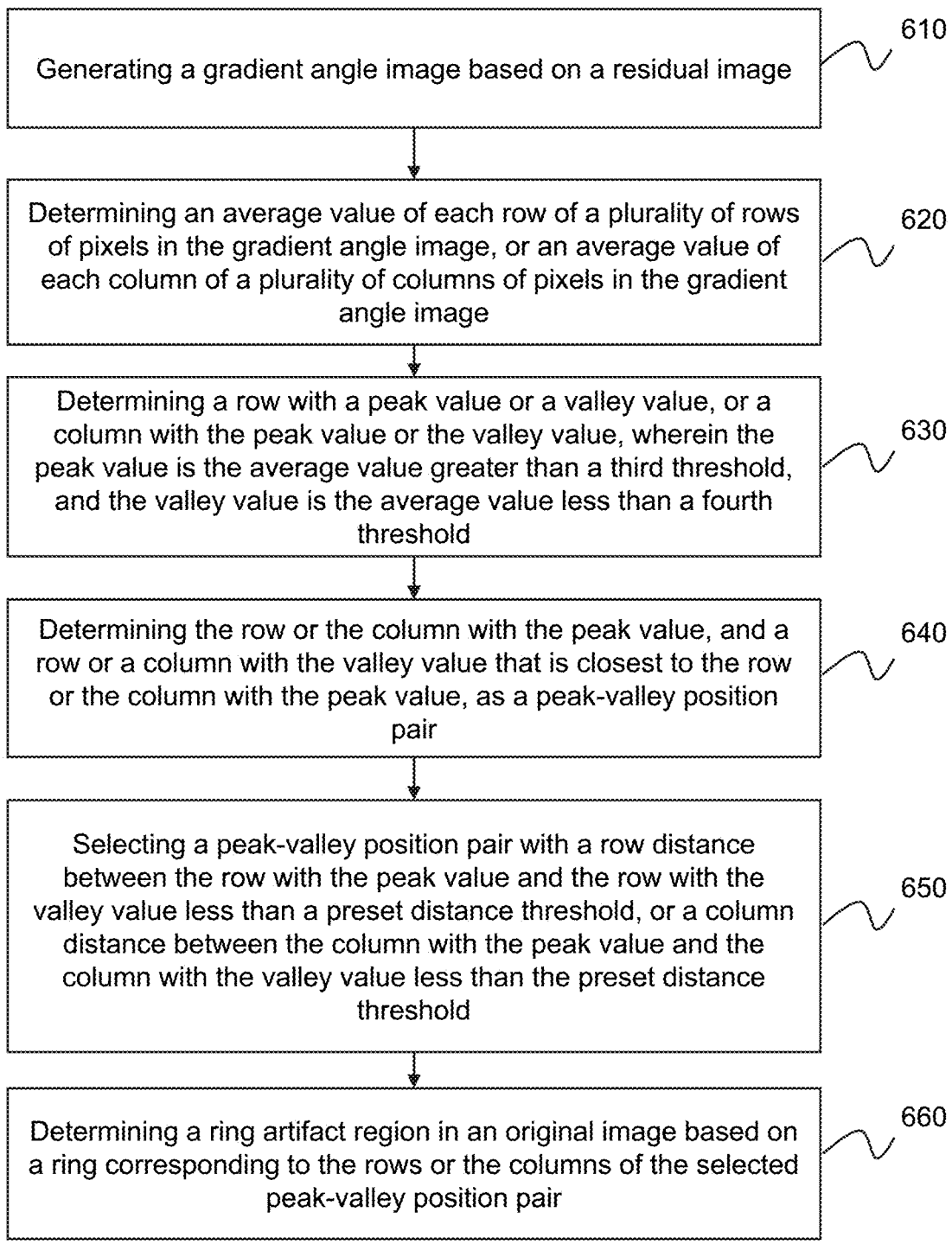
FIG. 6 is flowchart illustrating an exemplary process for determining a location of a ring artifact according to some embodiments of the present disclosure.

FIG. 6 is flowchart illustrating an exemplary process 600 for determining a location of a ring artifact according to some embodiments of the present disclosure. Specifically, process 600 for determining the location of the ring artifact may be executed by the processing device 140. For example, process 600 for determining the location of the ring artifact may be stored in a storage device (e.g., storage device 150, storage 220) in the form of a program or an instruction. When the imaging system 100 (e.g., the processing device 140) executes the program or the instruction, process 600 for determining the location of the ring artifact may be implemented. As shown in FIG. 6, process 600 for determining the location of the ring artifact may include:

In 610, a gradient angle image may be generated based on a residual image. Specifically, operation 610 may be performed by the ring artifact determination module 360.

In some embodiments, the generating the gradient angle image based on the residual image may include obtaining the gradient angle image by determining a gradient angle value of each pixel of a plurality of pixels in the residual image. In some embodiments, the gradient angle value of the pixel in the residual image may be determined according to a gradient angle function. The gradient angle value may reflect a ratio of a change in pixel values along each of at least two different directions in the residual image. In some embodiments, the gradient angle function may include:

$$Gdir = \sin\left(\tan^{-1}\left(\frac{\partial I/\partial y}{\partial I/\partial x}\right)\right), \quad (1)$$

where I refers to a pixel value in a residual image; y refers to a column direction of a residual image matrix; and x refers to a row direction of the residual image matrix.

Figure 12:
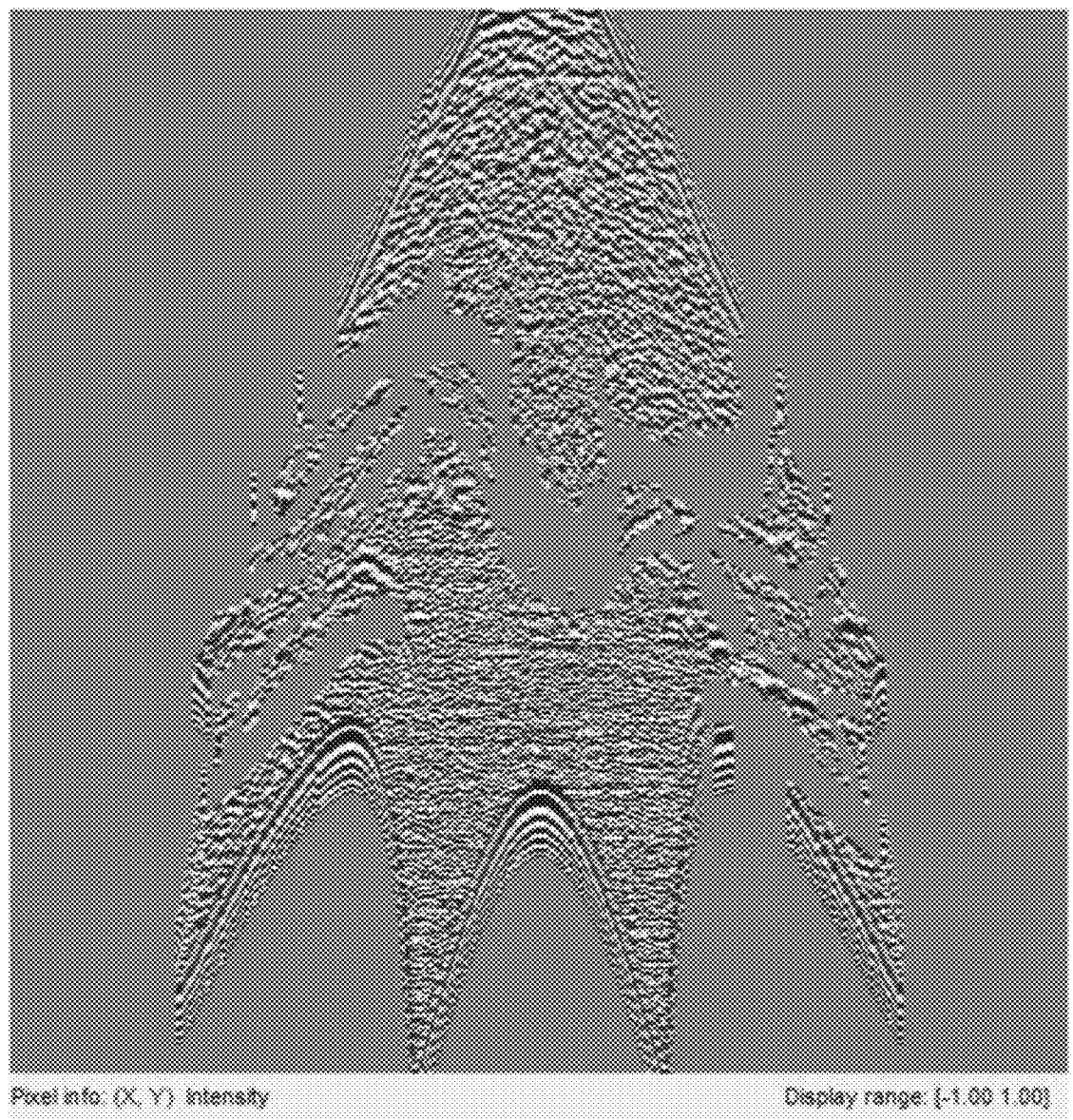
FIG. 12 is a schematic diagram illustrating a gradient angle image according to some embodiments of the present disclosure.

Merely by way of example, the ring artifact determination module 360 may generate the gradient angle image (as shown in FIG. 12) based on the residual image (as shown in FIG. 11), and the trapezoidal region in the gradient angle image may have a plurality of pixels.

In some embodiments, an instruction to generate the gradient angle image may be stored in a storage device (e.g., storage device 150, storage 220), and may be retrieved by processing device 140 (e.g., the ring artifact determination module 360).

In 620, an average value of each row of a plurality of rows of pixels in the gradient angle image, or an average value of each column of a plurality of columns of pixels in the gradient angle image may be determined. Specifically, operation 620 may be performed by the ring artifact determination module 360.

In some embodiments, the ring artifact determination module 360 may determine the average value of the each row of the plurality of rows in the gradient angle image, or the average value of the each column of the plurality of columns in the residual image. In some embodiments, the average value may include an arithmetic mean value, a weighted mean value, or an operation value obtained by other determination methods (e.g., a median value, a region mean value obtained after fitting).

Figure 13:
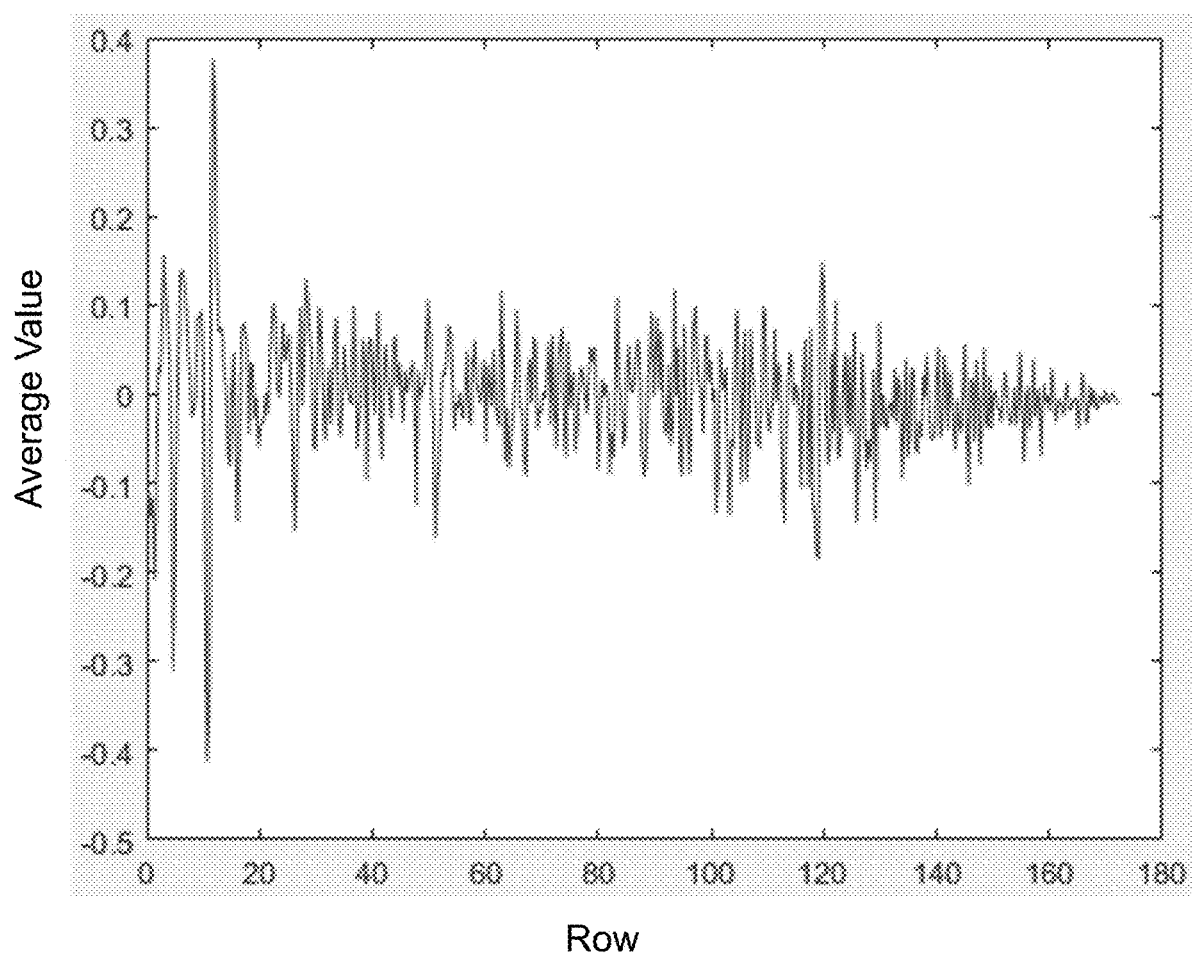
FIG. 13 is a schematic diagram illustrating an average pixel value image according to some embodiments of the present disclosure.

In some embodiments, the ring artifact determination module 360 may also normalize the average value of the each row or the average value of the each column. For example, the average value of the each row or the average value of the each column may be normalized to a specified range. The specified range may be between ±0.5, ±1, or ±2.5. Merely by way of example, the ring artifact determination module 360 may determine the average value of the each row in the gradient angle image (as shown in FIG. 12), and then normalize the average value of the each row to obtain a graph as shown in FIG. 13. As shown in FIG. 13, an abscissa may be a row number. It may be understood that the row number corresponds to a radius of the potential ring. An ordinate may be an average value of pixel values of the corresponding row. It may be understood that the average value is proportional to or positively correlates with the appearance probability of the artifact ring at the location of the ring in the original image corresponding to the row.

In some embodiments, an instruction to determine the average value of the each row or the average value of the each column in the residual image may be stored in a storage device (e.g., storage device 150, storage 220), and may be retrieved by the processing device 140 (e.g., the ring artifact determination module 360).

In 630, a row with a peak value or a valley value, or a column with the peak value or the valley value may be determined. The peak value may be the average value greater than a third threshold, and the valley value may be the average value less than a fourth threshold. Specifically, operation 630 may be performed by the ring artifact determination module 360.

Take a result of determining the average value of the each row as an example. It should be understood that, in some embodiments, for example, the rows in the original image may be mapped to the columns in the polar coordinate image. The row or the column with the peak value or the valley value may be determined based on the average value of the each row. Specifically, in some embodiments, determining the row with the peak value or the valley value may include determining the row or the column in gradient angle image whose average value is greater than the third threshold or less than the fourth threshold. In some embodiments, the third threshold and the fourth threshold may be preset by an operator (e.g., a doctor) based on experiences. In some embodiments, absolute values of the third threshold and the fourth threshold may be the same, and the two thresholds may be opposite numbers. In some embodiments, the count of peak values greater than the third threshold may be one or more. In some embodiments, the count of valley values less than the fourth threshold may be one or more.

Figure 14:
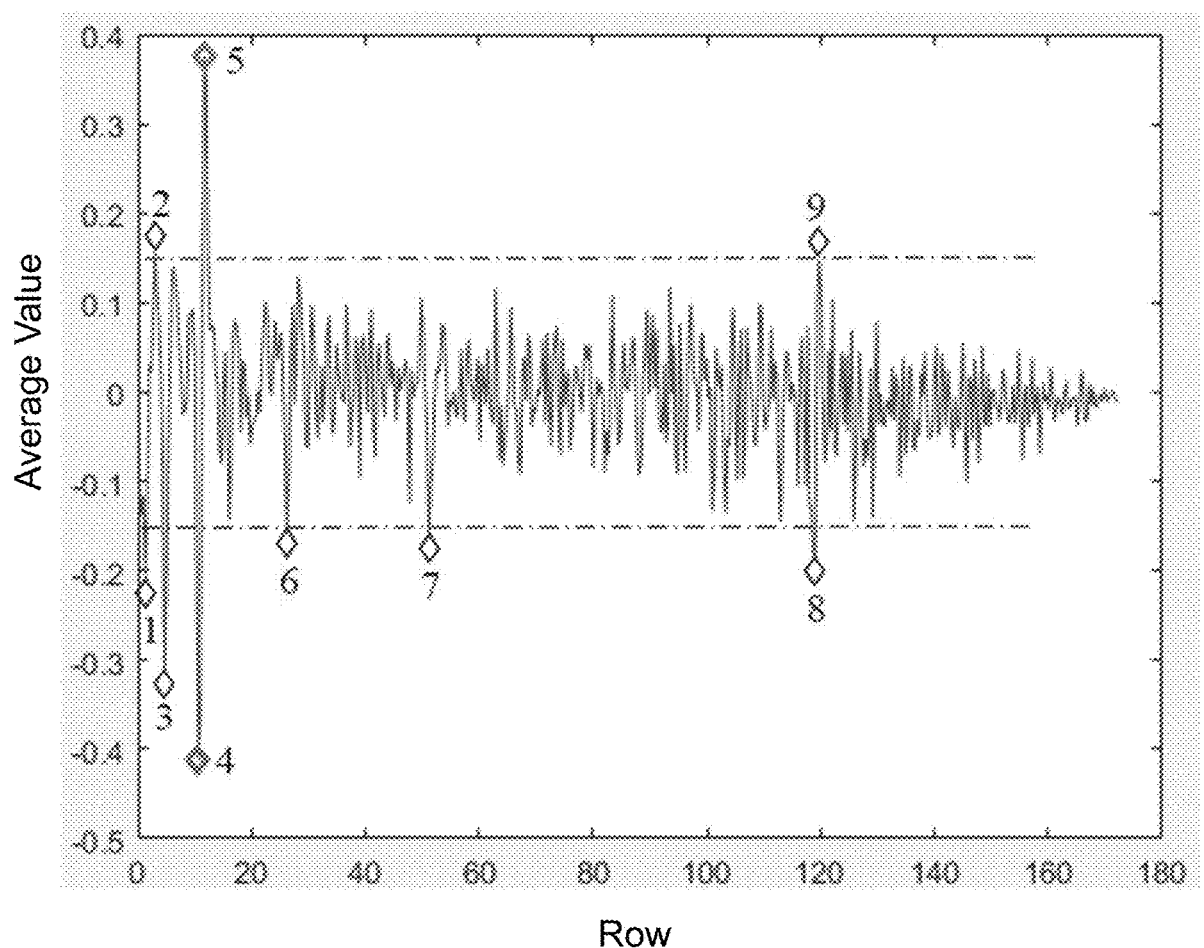
FIG. 14 is a schematic diagram illustrating a peak-valley position pair image according to some embodiments of the present disclosure.

Merely by way of example, as shown in FIG. 14, the third threshold may be set as 0.15, and the fourth threshold may be set as −0.15. The ring artifact determination module 360 may determine the peak value greater than the third threshold (e.g., a point 2, a point 5, a point 9) and the valley value less than the fourth threshold (e.g., a point 1, a point 3, a point 4, a point 6, a point 7, a point 8), and determine the rows corresponding to the peak values and the valley values.

In some embodiments, an instruction to determine the row or the column with the peak value or the valley value may be stored in a storage device (e.g., the storage device 150, the storage 220), and may be retrieved by the processing device 140 (e.g., the ring artifact determination module 360).

In 640, the row or the column with the peak value, and a row or a column with the valley value that is closest to the row or the column with the peak value may be determined as a peak-valley position pair. Specifically, operation 640 may be performed by the ring artifact determination module 360.

In some embodiments, a distance between the row or the column with the peak value and the row or the column with the valley value (a distance between horizontal axis coordinates corresponding to the peak value and the valley value shown in FIG. 14) may reflect a width of a potential artifact ring in the original image. The following description is taken rows as an example.

In some embodiments, the count of valley values close to the peak value may be 0, 1, or 2. For example, the valley values close to the point 5 may include the point 4 and the point 6 as illustrated in FIG. 14. As another example, the valley values close to the point 9 may include the point 8 as illustrated in FIG. 14. In some embodiments, the peak value and the valley value that is closest to the peak value may be selected as a peak-valley position pair. In some embodiments, the count of peak-valley position pairs may include one or more. Merely by way of example, as shown in FIG. 14, the point 2 and the point 3 may be regarded as a peak-valley position pair, the point 5 and the point 4 may be regarded as a peak-valley position pair, and the point 8 and the point 9 may be regarded as a peak-valley position pair as shown in FIG. 14. Further, the rows corresponding to the peak-valley position pair may be regarded as a peak-valley position pair. For example, as shown in FIG. 14, the rows corresponding to the point 2 and the point 3 may be regarded as the peak-valley position pair, the rows corresponding to the point 5 and the point 4 may be regarded as the peak-valley position pair, and the rows corresponding to the point 8 and the point 9 may be regarded as the peak-valley position pair.

In some embodiments, an instruction to determine the peak-valley position pair may be stored in a storage device (e.g., storage device 150, storage 220), and may be retrieved by the processing device 140 (e.g., the ring artifact determination module 360).

In 650, a peak-valley position pair with a row distance between the row with the peak value and the row with the valley value less than a preset distance threshold, or a column distance between the column with the peak value and the column with the valley value less than the preset distance threshold may be selected. Specifically, operation 650 may be performed by the ring artifact determination module 360.

It should be understood that the distance between the row or the column with the peak value and the row or the column with the valley value (the distance between horizontal axis coordinates corresponding to the peak value and the valley value shown in FIG. 14) may reflect the width of the potential artifact ring in the original image. When the distance is relatively large, a location corresponding to the peak-valley position pair in the original image may not be an artifact ring. The peak-valley position pair may be caused by noise pollution. In some embodiments, the preset distance threshold may be preset by an operator (e.g., a doctor) based on experiences. In some embodiments, the ring artifact determination module 360 may select the peak-valley position pair with the row distance or the column distance less than the preset distance threshold. It should be understood that, when the row distance or the column distance meets a condition, such as less than the preset distance threshold, the location in the original image corresponding to the peak-valley position pair may be the artifact ring. Therefore, the peak-valley position pair may need to be selected. In some embodiments, the count of selected peak-valley position pairs may be one or more. Merely by way of example, as shown in FIG. 14, the ring artifact determination module 360 may select the point 5 and the point 4 as an effective peak-valley position pair based on the preset distance threshold, and select the point 8 and the point 9 as another effective one peak-valley position pair. The distance between the abscissa of the point 2 and the abscissa of the point 3 may be greater than the preset distance threshold, and cannot be regarded as an effective peak-valley position pair.

In some embodiments, an instruction to select the peak-valley position pair may be stored in a storage device (e.g., the storage device 150, the storage 220), and may be retrieved by the processing device 140 (e.g., the ring artifact determination module 360).

In 660, a ring artifact region in the original image may be determined based on a ring corresponding to the rows or the columns of the selected peak-valley position pair. Specifically, operation 660 may be performed by the ring artifact determination module 360.

In some embodiments, the count of rows or columns in the selected peak-valley position pairs may include one or more. For example, as shown in FIG. 14, two peak-valley position pairs may be selected. The two peak-valley position pairs may correspond to four rows in the gradient angle image, and two rings in the original image. That is, the ring artifact region may include two ring artifacts. In some embodiments, the ring artifact may be a bright ring or a dark ring with a certain width. Specifically, as shown in FIG. 14, the distance between the abscissa of the peak-valley position pair of the point 4 and the point 5 may positively correlate with the width of the artifact ring in the original image, the point 4 may correspond to a boundary from light to dark on the ring artifact in the original image, the point 5 may correspond to the boundary from dark to bright on the ring artifact in the original image, and the artifact ring may be a dark ring.

In some embodiments, an instruction to determine the ring artifact region may be stored in a storage device (e.g., the storage device 150, the storage 220), and may be retrieved by the processing device 140 (e.g. the ring artifact determination module 360).

It should be noted that process 600 and the description is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the gradient angle function in operation 610 may have other functional forms. As another example, in operation 620, the average value of pixel values of the each row or the each column are not normalized, and the average value may be directly used in subsequent processing operations.

The benefits of the embodiments of the present disclosure may include but are not limited to: (1) An original image may be mapped to a polar coordinate image for processing, which may simplify the image processing process. (2) The original image may be mapped to a trapezoidal region or a triangular region in the polar coordinate image, which may reduce the count of interpolation pixels relative to the entire polar coordinate image, and reduce the influence of noise. (3) A protection region may be segmented in the polar coordinate image and the protection region may not be processed, which may reduce the effect of pixels with a relatively high CT value on an artifact detection result, and improve the detection accuracy. (4) A gradient angle image may be used for processing, which may reduce the influence of noise. It should be noted that different embodiments may have different beneficial effects. In different embodiments, the beneficial effects may be any one or any combination of the above beneficial effects, or any other beneficial effects that may be obtained.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for determining a ring artifact, comprising:
obtaining an original image;
mapping a plurality of pixels in the original image to a polar coordinate image;
determining a protection region in the polar coordinate image, wherein determining the protection region in the polar coordinate image comprises processing the polar coordinate image by
    obtaining a strong boundary region by performing a boundary extraction operation on the polar coordinate image; and
    generating the protection region by performing a region expansion operation on the strong boundary region;
smoothing at least one region in the processed polar coordinate image except the protection region to obtain a smooth image, wherein the smooth image includes the protection region;
generating a residual image based on the polar coordinate image and the smooth image; and determining a location of the ring artifact in the original image based on the residual image.

2. The method of claim 1, wherein mapping a plurality of pixels in the original image to a polar coordinate image comprises:
   determining a location of an imaging center in the original image;
   determining a plurality of rings centered on the location of the imaging center in the original image and from the imaging center and outward; and
   mapping the plurality of pixels on the plurality of rings to a plurality of lines corresponding to a plurality of rows of pixels or a plurality of columns of pixels in the polar coordinate image, respectively, wherein each of the plurality of rings corresponds to each of the plurality of rows or each of the plurality of columns.

3. The method of claim 2, wherein mapping the plurality of pixels on the plurality of rings to a plurality of lines corresponding to a plurality of rows of pixels or a plurality of columns of pixels in the polar coordinate image, respectively, comprises:
   for each ring of the plurality of rings,
   performing an interpolation operation on the plurality of pixels on the ring to obtain at least one interpolation pixel; and
   mapping the plurality of pixels on the ring and the at least one interpolation pixel to a line corresponding to a row of pixels or a column of pixels in the polar coordinate image.

4. The method of claim 2, wherein a length of a line positively correlates with a radius of a ring corresponding to the line.

5. The method of claim 1, wherein mapping a plurality of pixels in the original image to a polar coordinate image comprises:
   mapping the plurality of pixels in the original image to a trapezoidal region or a triangular region in the polar coordinate image.

6. The method of claim 1, wherein generating a residual image based on the polar coordinate image and the smooth image comprises:
   generating the residual image by subtracting a value of each pixel of a plurality of pixels in the polar coordinate image from a value of a corresponding pixel of a plurality of pixels in the smooth image.

7. The method of claim 1, wherein determining a location of the ring artifact in the original image based on the residual image comprises:
   determining an average value of each row of a plurality of rows of pixels in the residual image, or an average value of each column of a plurality of columns of pixels in the residual image; and
   determining a ring in the original image corresponding to a row or a column in the residual image whose average value is greater than a first threshold or below a second threshold as a ring artifact region.

8. The method of claim 1, wherein determining a location of the ring artifact in the original image based on the residual image comprises:
   generating a gradient angle image based on the residual image;
   determining an average value of one or more pixel values of each row of a plurality of rows of pixels in the gradient angle image, or an average value of one or more pixel values of each column of a plurality of columns of pixels in the gradient angle image;
   determining at least one row with a peak value or a valley value, or at least one column with the peak value or the valley value, wherein the peak value is the average value greater than a third threshold, and the valley value is the average value less than a fourth threshold;
   determining the at least one row or the at least one column with the peak value, and a row or a column with the valley value that is closest to the at least one row or the at least one column with the peak value, as at least one peak-valley position pair;
   selecting a peak-valley position pair, among the at least one peak-valley position pair, with a row distance between the row with the peak value and the row with the valley value less than a preset distance threshold, or a column distance between the column with the peak value and the column with the valley value less than the preset distance threshold;
   determining a ring artifact region in the original image based on a ring corresponding to the rows or the columns of the selected peak-valley position pair.

9. The method of claim 8, wherein generating a gradient angle image based on the residual image comprises:
   obtaining the gradient angle image by determining a gradient angle value of each pixel of a plurality of pixels in the residual image, wherein the gradient angle value reflects a ratio of a change in pixel values along each of at least two different directions in the residual image.

10. A system for determining a ring artifact comprising:
    an obtaining module, a mapping module, a protection region determination module, a smoothing module, a residual image generation module, and a ring artifact determination module, wherein:
    the obtaining module is configured to obtain an original image;
    the mapping module is configured to map a plurality of pixels in the original image to a polar coordinate image;
    the protection region determination module is configured to determine a protection region in the polar coordinate image, wherein to determine the protection region in the polar coordinate image, the protection region determination module is further configured to process the polar coordinate image by
      obtaining a strong boundary region by performing a boundary extraction operation on the polar coordinate image; and
      generating the protection region by performing a region expansion operation on the strong boundary region;
    the smoothing module is configured to smooth at least one region in the processed polar coordinate image except the protection region to obtain a smooth image, wherein the smooth image includes the protection region;
    the residual image generation module is configured to generate a residual image based on the polar coordinate image and the smooth image; and
    the ring artifact determination module is configured to determine a location of the ring artifact in the original image based on the residual image.

11. A system for determining a ring artifact, comprising:
    at least one storage device storing a set of instructions; and
    at least one processor in communication with the at least one storage device, when executing the stored set of instructions, the at least one processor causes the system to perform operations including:
obtaining an original image;
mapping a plurality of pixels in the original image to a polar coordinate image;
determining a protection region in the polar coordinate image, wherein determining the protection region in the polar coordinate image comprises processing the polar coordinate image by
obtaining a strong boundary region by performing a boundary extraction operation on the polar coordinate image; and
generating the protection region by performing a region expansion operation on the strong boundary region;
smoothing at least one region in the processed polar coordinate image except the protection region to obtain a smooth image, wherein the smooth image includes the protection region;
generating a residual image based on the polar coordinate image and the smooth image; and
determining a location of the ring artifact in the original image based on the residual image.

12. The system of claim 11, wherein mapping a plurality of pixels in the original image to a polar coordinate image comprises:
determining a location of an imaging center in the original image;
determining a plurality of rings centered on the location of the imaging center in the original image and from the imaging center and outward; and
mapping the plurality of pixels on the plurality of rings to a plurality of lines corresponding to a plurality of rows of pixels or a plurality of columns of pixels in the polar coordinate image, respectively, wherein each of the plurality of rings corresponds to each of the plurality of rows or each of the plurality of columns.

13. The system of claim 12, wherein mapping the plurality of pixels on the plurality of rings to a plurality of lines corresponding to a plurality of rows of pixels or a plurality of columns of pixels in the polar coordinate image, respectively, comprises:
for each ring of the plurality of rings,
performing an interpolation operation on the plurality of pixels on the ring to obtain at least one interpolation pixel; and
mapping the plurality of pixels on the ring and the at least one interpolation pixel to a line corresponding to a row of pixels or a column of pixels in the polar coordinate image.

14. The system of claim 12, wherein a length of a line positively correlates with a radius of a ring corresponding to the line.

15. The system of claim 11, wherein mapping a plurality of pixels in the original image to a polar coordinate image comprises:
mapping the plurality of pixels in the original image to a trapezoidal region or a triangular region in the polar coordinate image.

16. The system of claim 11, wherein generating a residual image based on the polar coordinate image and the smooth image comprises:
generating the residual image by subtracting a value of each pixel of a plurality of pixels in the polar coordinate image from a value of a corresponding pixel of a plurality of pixels in the smooth image.

17. The system of claim 11, wherein determining a location of the ring artifact in the original image based on the residual image comprises:
determining an average value of each row of a plurality of rows of pixels in the residual image, or an average value of each column of a plurality of columns of pixels in the residual image; and
determining a ring in the original image corresponding to a row or a column in the residual image whose average value is greater than a first threshold or below a second threshold as a ring artifact region.

18. The system of claim 11, wherein determining a location of the ring artifact in the original image based on the residual image comprises:
generating a gradient angle image based on the residual image;
determining an average value of one or more pixel values of each row of a plurality of rows of pixels in the gradient angle image, or an average value of one or more pixel values of each column of a plurality of columns of pixels in the gradient angle image;
determining at least one row with a peak value or a valley value, or at least one column with the peak value or the valley value, wherein the peak value is the average value greater than a third threshold, and the valley value is the average value less than a fourth threshold;
determining the at least one row or the at least one column with the peak value, and a row or a column with the valley value that is closest to the at least one row or the at least one column with the peak value, as at least one peak-valley position pair;
selecting a peak-valley position pair, among the at least one peak-valley position pair, with a row distance between the row with the peak value and the row with the valley value less than a preset distance threshold, or a column distance between the column with the peak value and the column with the valley value less than the preset distance threshold;
determining a ring artifact region in the original image based on a ring corresponding to the rows or the columns of the selected peak-valley position pair.

* * * * *